US006528250B1

(12) United States Patent
Montelaro et al.

(10) Patent No.: US 6,528,250 B1
(45) Date of Patent: Mar. 4, 2003

(54) EQUINE INFECTIOUS ANEMIA CHALLENGE MODEL FOR TESTING VACCINES, DIAGNOSTICS AND TREATMENTS

(75) Inventors: Ronald Montelaro, Wexford, PA (US); Bridget Puffer, Corning, NY (US); Feng Li, Philadelphia, PA (US); Charles Issel, Lexington, KY (US); Kristina J. Hennessey, Parkville, MO (US); Karen K. Brown, Parkville, MO (US)

(73) Assignee: Akzo Nobel N.V., Arnhem (NL)

( * ) Notice: Subject to any disclaimer, the term of this patent is extended or adjusted under 35 U.S.C. 154(b) by 0 days.

(21) Appl. No.: 09/659,030

(22) Filed: Sep. 9, 2000

(51) Int. Cl.[7] ........................ A61K 48/00; A61K 39/21; A61K 121/00; A61K 123/00; C12Q 1/70

(52) U.S. Cl. ........................ 435/5; 424/93.1; 424/93.2; 424/187.1; 424/188; 424/9.2; 435/69.1; 435/91.33; 345/536; 345/23.72

(58) Field of Search .......................... 424/187.1, 188.1, 424/93.1, 93.2, 9.2; 435/5, 69.1, 91.33; 345/536, 23.72

(56) References Cited

PUBLICATIONS

Harrold et al. J. Virol. 2000, vol. 74, pp. 3112–3121.*

Hammond et al. J. Virol. 1997, vol. 71, pp. 3840–3852.*

Payne et al. J. Virol. 1998, vol. 72, pp. 483–487.*

Cook et al. J. Virol. 1998, vol. 72, pp. 1383–1393.*

Clabough et al. J. Virol. 1991, vol. 65, pp. 6242–6252.*

Salinovich, Olivia et al.: "Rapid Emergence of Novel Antigenic and Genetic Cariants of Equine infectious Anemia Virus during Persistent Infection", Virology, Jan. 1986, p. 71–80, vol. 57, No. 1.

Hussain, K. A., et al.: "Antigenic mapping of the envelope proteins of equine infectious anemia virus: identification of a neutralization domain and a conserved region on glycoprotein 90", Archives Of Virology, 1998, p. 213–234.

Issel, C.J., et al.: "Efficacy of Inactivated Whole–Virus and Subunit Vaccines in Preventing Infection and Disease Caused by Equine Infectious Anemia Virus", *Virology*, Jun. 1992, p. 3398–3408, vol. 66, No. 6.

Orrego, Alberto et al.: "Virulence and in vitro growth of a cell–adapted strain of equine infectious anemia virus after serial passage in ponies", American Journal Of Veterinary Research, 1982, p. 1556–1560, vol. 43, No. 9.

Leroux, Caroline et al.: "Equine Infectious Anemia Virus Genomic Evolution in Progressor and Nonprogressor Ponies", Virology, May 2001, p. 4570–4583, vol. 75, No. 10.

Hammond, Scott A. et al.: "Maturation of the Cellular and Humoral Immune Responses to Persistent Infection in Horses by Equine Infectious Anemia Virus is a Complex and Lengthy Process", Virology, May 1997, p. 3840–3852, vol. 71, No. 5.

Cook, R. Frank et al.: "Development and Characterization of an In Vivo Pathogenic Molecular Clone of Equine Infectious Anemia Virus", Virology, Feb. 1998, p. 1383–1393, vol. 72, No. 2.

Leroux, Caroline et al.: "Novel and Dynamic Evolution of Equine Infectious Anemia Virus Genomic Quasispecies Associated with Sequential Disease Cycles in an Experimentally Infected Pony", Virology, Dec. 1997, p. 9627–9639, vol. 71, No. 12.

Langemeier, John L., et al.: "Detection of Equine Infectious Anemia Viral RNA in Plasma Samples from Recently Infected and Long–Term Inapparent Carrier Animals by PCR", Journal Of Clinical Microbiology, Jun. 1996, p. 1481–1487, vol. 34, No. 6.

Lichtenstein, Drew L., et al.: "Genomic Quasispecies Associated with the Initiation of Infection and Disease in Ponies Experimentlly Infected with Equine Infectious Anemia Virus", Virology, Jun. 1996, p. 3346–3354, vol. 70, No. 6.

Lichtenstein, Drew L., et al.: "Replication In Vitro and In Vivo of and Equine Infectious Anemia Virus Mutant Deficient in dUTPase Activity", Virology, May 1995, p. 2881–2888, vol. 69, No. 5.

Ball, Judith M., et al.: "Detailed Mapping of the Antigenicity of the Surface Unit Glycoprotein of Equine Infectious Anemia Virus by Using Synthetic Peptide Strategies", Virology, Feb. 1992, p. 732–742, vol. 66, No. 2.

Montelaro, Ronald C., et al.: "Antigenic Variation during Persistent Infection by Equine Infectious Anemia Virus, a Retrovirus", Journal of Biological Chemistry, Aug. 1984, p. 10539–10544, vol. 259, No. 16.

Issel, Charles J., et al.: "A Perspective on Equine Infectious Anemia with an Emphasis on Vector Transmission and Genetic Analysis", Veterinary Microbiology, 1998, p. 251–286.

Ball, Judith M., et al.: "EIAV Genomic Organization: Further Characterization by Sequencing of Purified Glycoproteins and cDNA", Virology, 1988, p. 601–605.

Issel, Charles J., et al.: "Evolution of Equine Infectious Anemia Diagnostic Tests: Recognition of a Need for Detection of Anti–EIAV Glycoprotein Antibodies", p. 196–200.

(List continued on next page.)

*Primary Examiner*—Ali R. Salimi
*Assistant Examiner*—Bao Qun Li
(74) *Attorney, Agent, or Firm*—William P. Ramey, III; William M. Blackstone

(57) ABSTRACT

The invention relates to a method for infecting equines with an equine infectious anemia virus (EIAV) in order to reproduce a natural infection challenge model. More specifically, the invention provides a multiple low dose equine EIA challenge model comprising administering at least 1 median horse infective dose to an equine using an intravenous route of administration. It is preferable that the EIAV be administered on a repeated basis. The multiple low dose EIA challenge model described herein can be used for testing efficacy of vaccines, treatments and diagnostic tests.

15 Claims, 8 Drawing Sheets

OTHER PUBLICATIONS

Rwambo, P.M., et al.: "In vitro isolation of a neutralization escape mutant of equine infectious anemia virus (EIAV)", Archives Of Virology, 1990, p. 275–280.

Rwambo, P.M., et al.: "Equine infectious anemia virus (EIAV) Humoral responses of recipient ponies and antigenic variation during persistent infection", Archives Of Virology, 1990, p. 199–212.

Newman, Mark J., et al.: "Transient Suppression of Equine Immune Responses by Equine Infectious Anemia Virus (EIAV)", Virology, May 1991, p. 55–66.

Montelaro, Ronald C., et al.: "Immunologic management of equine infectious anemia virus: a model for AIDS vaccine development", Eds. H. Schellekens and M.C. Horzinek Animal models in AIDS, 1990 Elsevier Science Publishers B.V. (Biomedical Division) p. 221–232.

Hammond, Scott A., et al.: "Immune Responses and Viral Replication in Long–Term Inapparent Carrier Ponies Inoculated with Equine Infectious Anemia Virus", Virology, Jul. 2000, p. 5968–5981, vol. 74, No. 13.

Tencza, Sarah B., et al.: "Development of a Fluorescence Polarization–Based Diagnostic Assay for Equine Infectious Anemia Virus", Journal Of Clinical Microbiology, May 2000, p. 1854–1859, vol. 38, No. 5.

Harrold, Sharon M., et al.: "Tissue Sites of Persistent Infection and Active Replication of Equine Infectious Anemia Virus during Acute Disease and Asymptomatic Infection in Experimentally Infected Equids", Virology, Apr. 2000, p. 3112–2121, vol. 74, No. 7.

Li, Feng, et al.: "The S2 Gene of Equine Infectious Anemia Virus Is a Highly Conserved Determinant of Viral Replication and Virulence Properties in Experimentally Infected Ponies", Virology, Jan. 2000, p. 573–579, vol. 74, No. 1.

Wang, S.Z.–S., et al.: "Enhancement of EIAV Replication and Disease by Immunization with a Baculovirus–Expressed Recombinant Envelope Surface Glycoprotein", Virology, 1994, p. 247–251.

Costa, L.R., et al.: "Response of Ponies to Challenge with Equine Infectious Anaemia Virus Following Exposure to Recombinant gp90 or Viral p26 Immunogens", Equine Infectious Diseases VII, p. 85–94.

Grund, Christian H., et al.: "Fine specificity of equine infectious anaemia virus gp90–specific antibodies associated with protective and enhancing immune responses in experimentally infected and immunized ponies", Journal Of General Virology, 1996, p. 435–442.

Montelaro, Ronald C., et al.: "Vaccines against Retroviruses", The Retroviridae, vol. 4, 1995, Chapter 8, p. 605–656.

Hammond, Scott A., et al.: "Evaluation of Antibody Parameters as Potential Correlates of Protection or Enhancement by Experimental Vaccines to Equine Infectious Anemia Virus", Virology, 1999, p. 416–430.

Raabe, Michelle L., et al.: "In Vitro Antibody–Dependent Enhancement Assays Are Insensitive Indicators of in Vivo Vaccine Enhancement of Equine Infectious Anemia Virus", Virology, 1999, p. 416–427.

Hammond, Scoctt A., et al.: "A Particulate Viral Protein Vaccine Reduces Viral Load and Delays Progression to Disease in Immunized Ponies Challenged with Equine Infectious Anemia Virus", Virology, 1999, p. 37–49.

Li, Feng, et al.: The S2 Gene of Equine Infectious Anemia Virus Is Dispensable for Viral Replication In Vitro, Virology, Oct. 1998, p. 8344–8348, vol. 72, No. 10.

Raabe, Michelle, et al.: Immunization with a Recombinant Envelope Protein (rgp90) of EIAV Produces a Spectrum of Vaccine Efficacy Ranging from Lack of Clinical Disease to Severe Enhancement, Virology, 1998, p. 151–162.

Payne, S.L., et al.: "Characterization of infectious molecular clones of equine infectious anaemia virus", Journal Of General Virology, 1994, p. 425–429.

Virology, 161, pp. 321–331, Payne et al Antigenic Variation and Lentrivirus Persistence: Variations in Envelope Gene Sequences during EIAV Infection Resemble Changes Reported for Sequential Isolates of HIV (month unavailable) 1987.

Li et al, J. Virol., Oct. 1998, pp. 8344–8348, The S2 Gene of Equine Infectious Anemia Virus Is Dispensable for Viral Replication In Vitro.

Lichtenstein et al, J. Virol., May 1995, pp. 2881–2888, Replication In Vitro and Vivo of an Equine Infectious Anemia Virus Mutant Deficient in dUTPase Activity.

Issel et al, Jun. 1992, pp. 3398–3408, Efficacy of Inactivated Whole–Virus and Subunit Vaccines in Preventing Infection and Disease Caused by Equine Infectious Anemia Virus.

* cited by examiner

Figure 1. Schematic diagrams of replication competent EIA viruses and Constructs
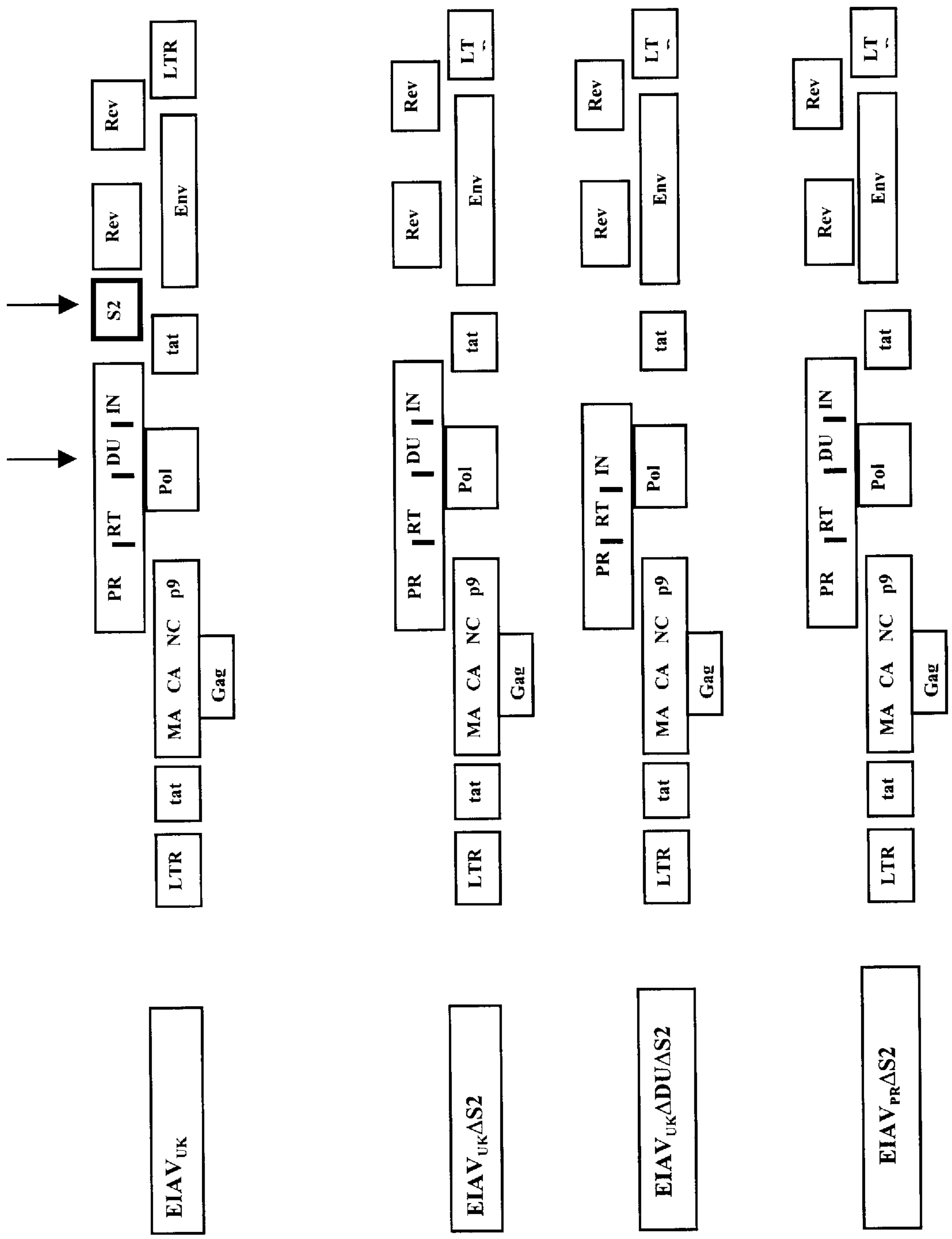

Figure 2a Schematic representation of EIA virus S2 gene and mutant clones derived from $EIAV_{UK}$. The EIA proviral DNA is shown at the top; the complete deduced amino acid sequence of the putative S2 protein is shown in single letter amino acid code at the bottom. Stop codons (indicated by arrows) were introduced into various positions in the EIA virus S2 gene to generate the specific mutant virus strains.

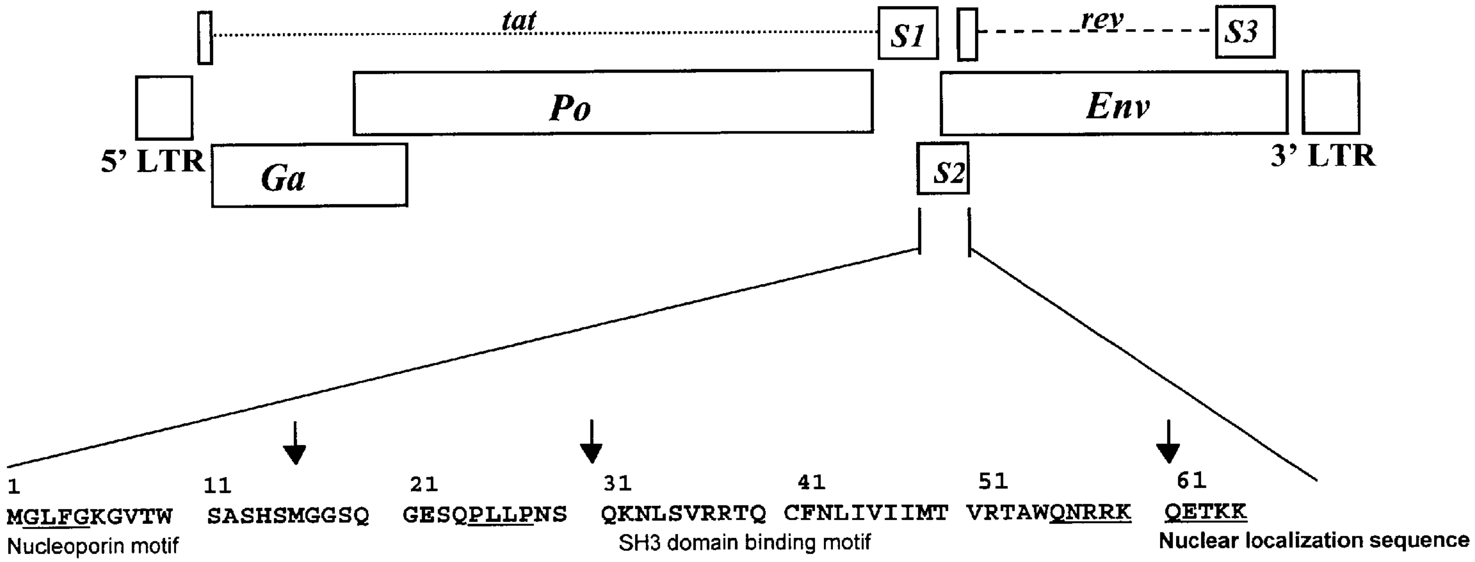

EIAV.G5/s Stop codon replaced amino acid $G^5$

EIAV.2M/X $M^{16}$ changed to T
Stop codons replaced $G^5$ and $G^{18}$

**EIAV.Δ*S2* Deletion of initial 5 nucleotides of *S2***

**Figure 2b Schematic representation of the Wild-type EIAV *S2* gene compared with the Δ *S2* gene of EIAV.2M/X (EIAV$_{UK}$ΔS2)**

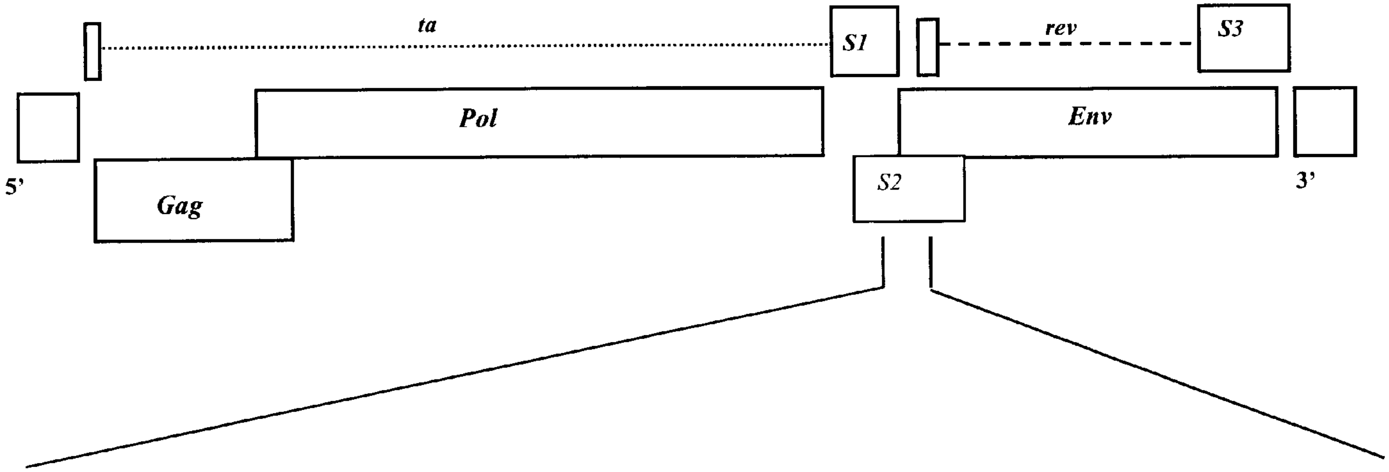

Wild type

ATG GGA TTA TTT GGT AAA GGG GTA ACA TGG TCA GCA TCG CAT TCT ATG GGG GGA TCC CAG GGG GAA TCT CAA
M G L F G K G V T W S A S H S M G G S Q G E S Q
CCC CTA TTA CCC AAC AGT CAG AAA AAT CTA AGT GTG AGG AGA ACA CAA TGT TTC AAC CTT ATT GTT ATA ATA
P L L P N S Q K N L S V R R T Q C F N L I V I I
ATG ACA GTA AGA ACA GCA TGG CAG AAT CGA AGG AAG CAA GAG ACC AAG AAA
M T V R T A W Q N R R K Q E T K K

Δ*S2*

ATG GGA GTA TAC TAG TGT AAA GGG GTA ACA TGG TCA GCA TCG CAT TCT ACG GGG TGA TCC CAG GGG GAA TCT
M G V Y • C K G V T W S A S H S T G • S Q G E S
CAA CCC CTA TTA CCC AAC AGT CAG AAA AAT CTA AGT GTG AGG AGA ACA CAA TGT TTC AAC CTT ATT GNT ATA
Q P L L P N S Q K N L S V R R T Q C F N L I V I
ATA ATG ACA GTA AGA ACA GCA TGG CAG AAT CGA AGG AAG CAA GAG ACC AAG AAA
I M T V R T A W Q N R R K Q E T K K

Figure 3a Circular Map of Biological Proviral Clone $EIAV_{PR}$
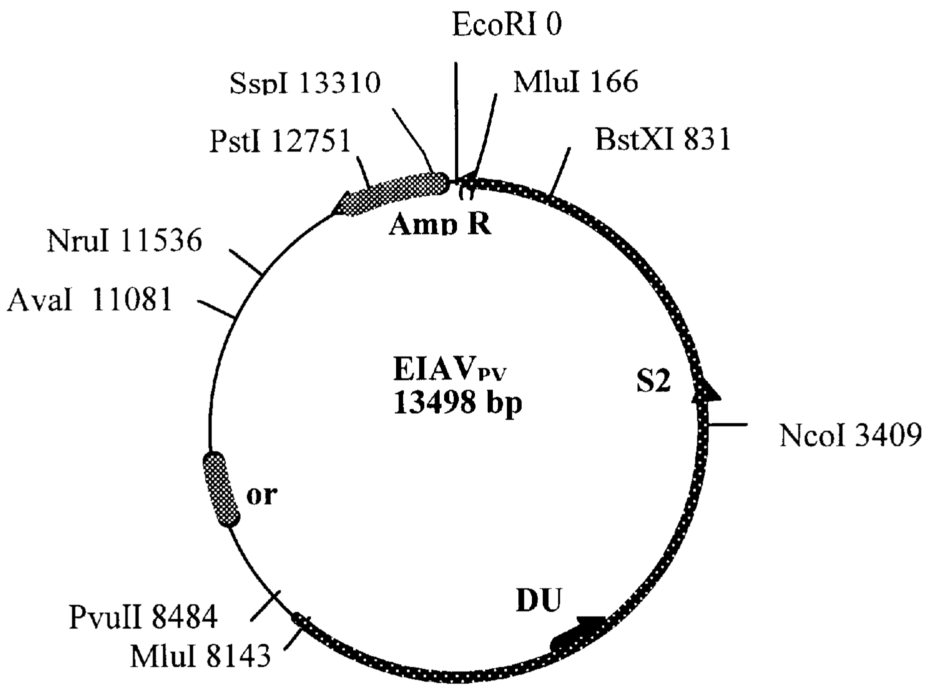
Figure 3b Circular Map of Molecular Infectious Clone $EIAV_{UK}$
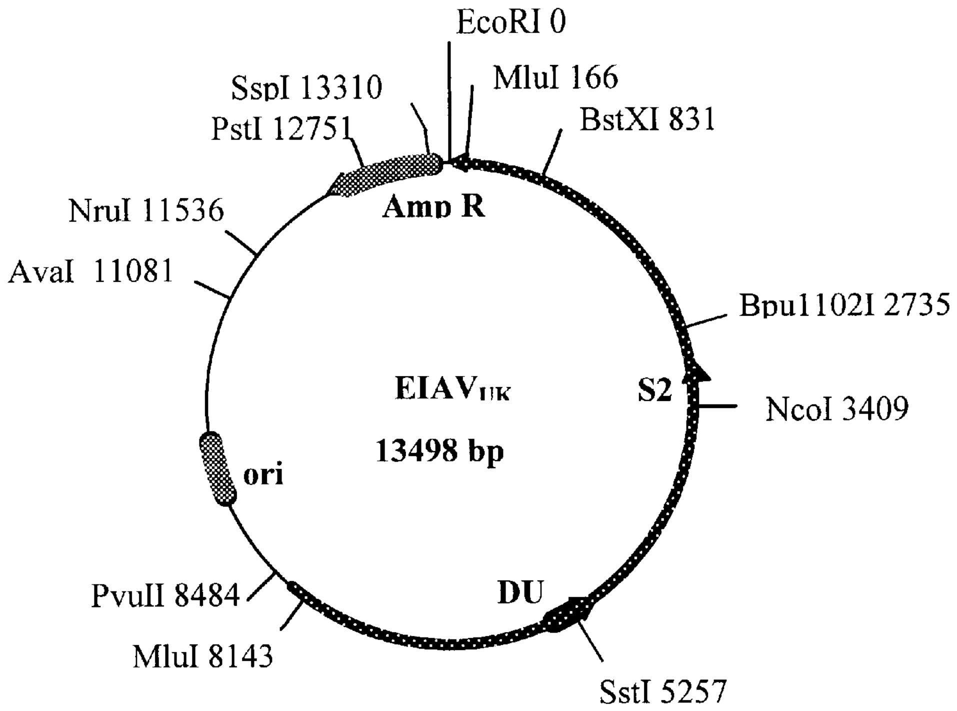

Figure 3c Circular Map of EIAV$_{UK}$ΔS2
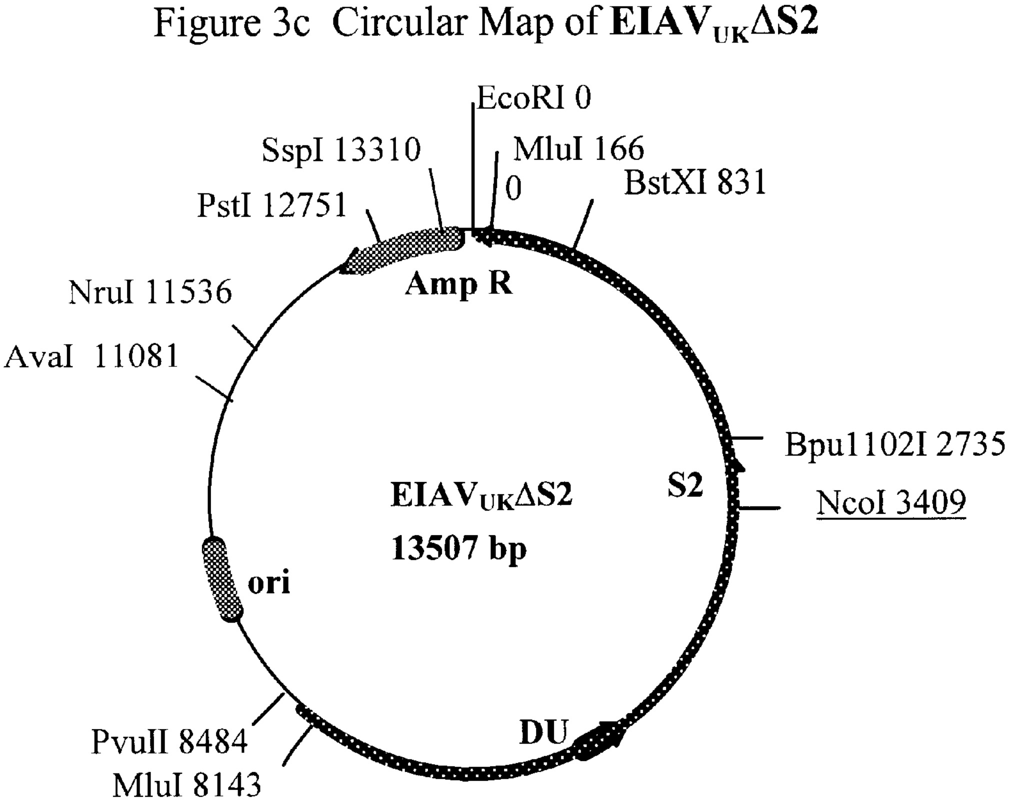
Figure 3d Circular map of EIAV$_{PR}$ΔS2
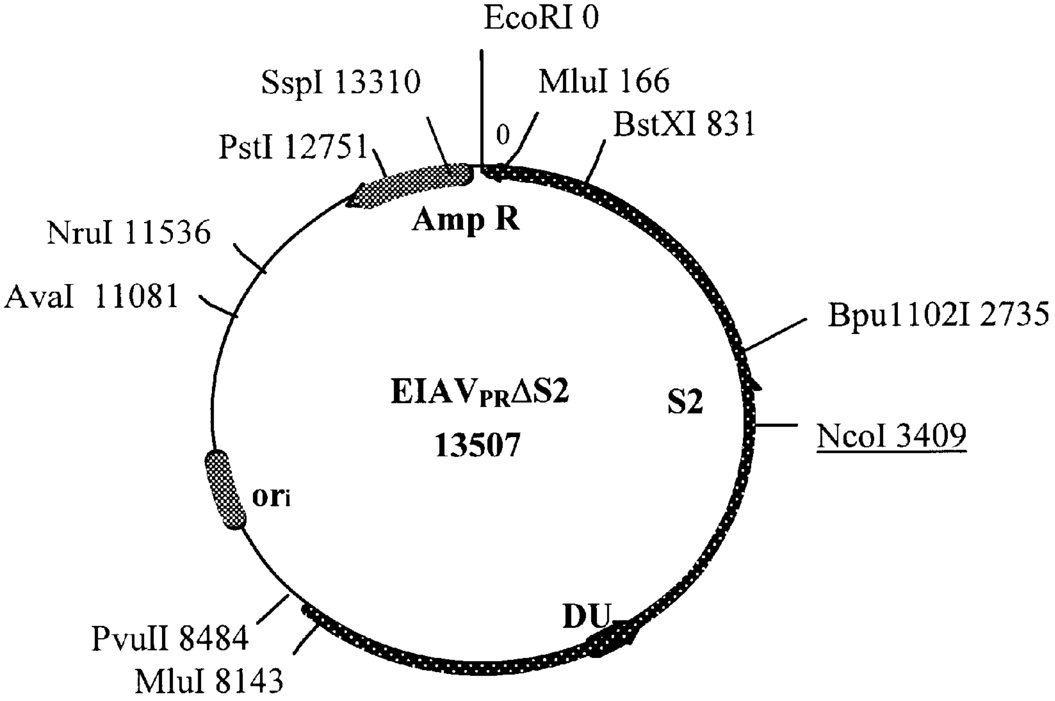

Figure 3e Circular Map of EIAV$_{UK}$ ΔDUΔS2
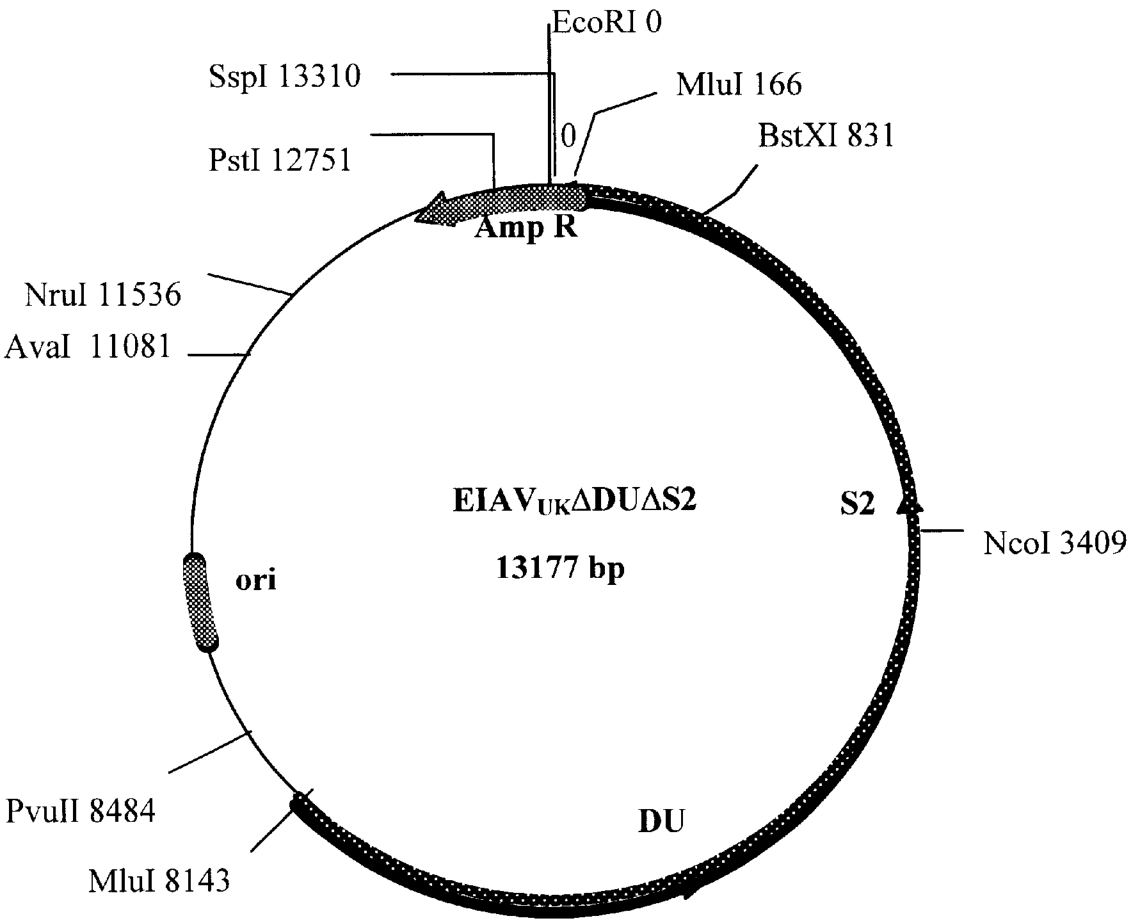
- EcoRI 0
- SspI 13310
- MluI 166
- PstI 12751
- BstXI 831
- Amp R
- NruI 11536
- AvaI 11081
- EIAV$_{UK}$ΔDUΔS2
- 13177 bp
- S2
- NcoI 3409
- ori
- PvuII 8484
- MluI 8143
- DU Figure 4 Replication of EIA Virus Mutant Clones *in vitro*
A
Replication in ED Cell Line
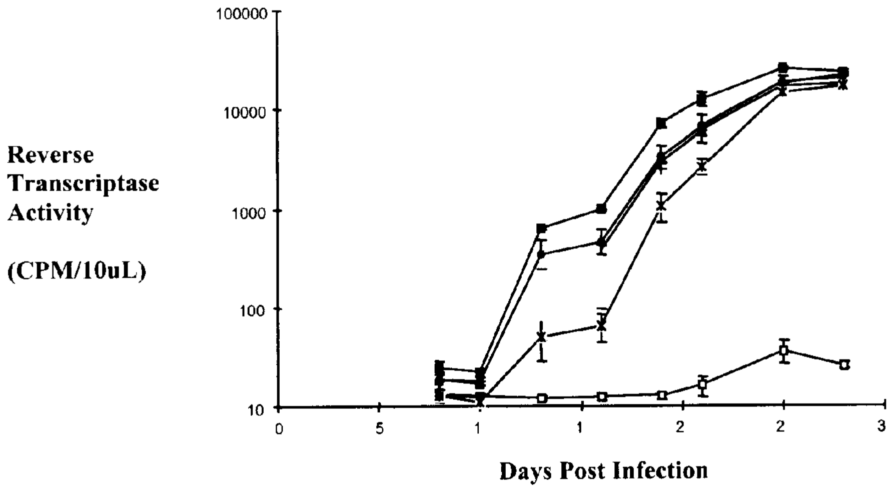
B
Replication in MDM Cells
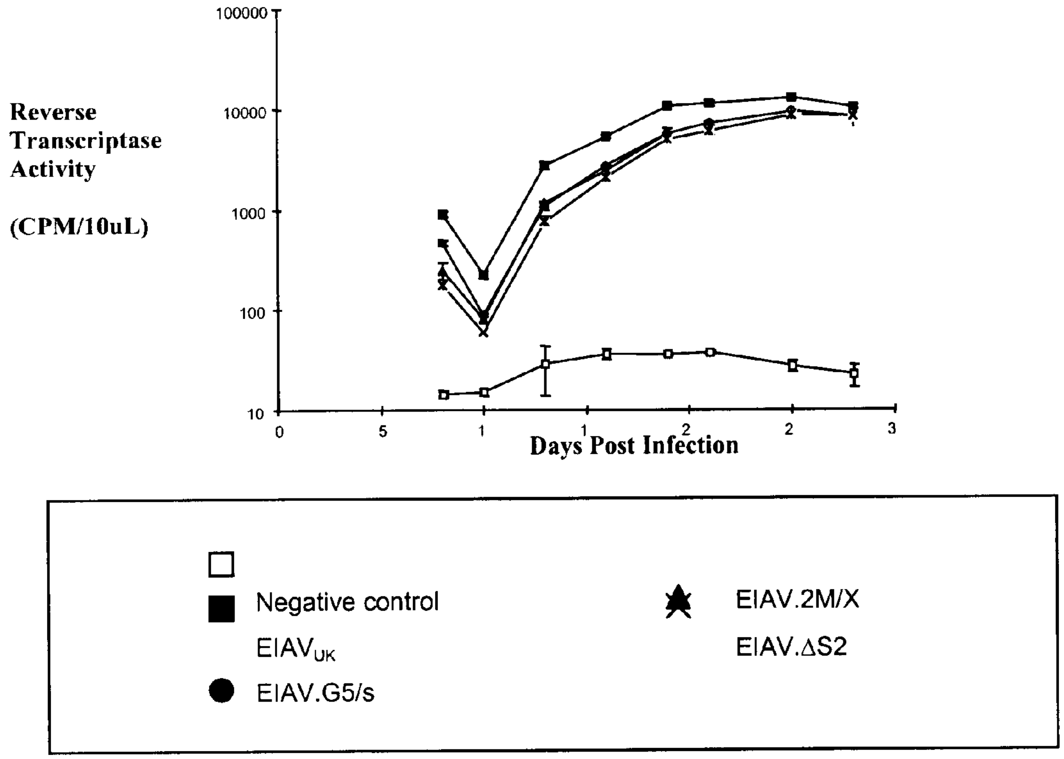

Figure 5 Schematic Representation of the *DU* gene and construction of EIAVΔDU
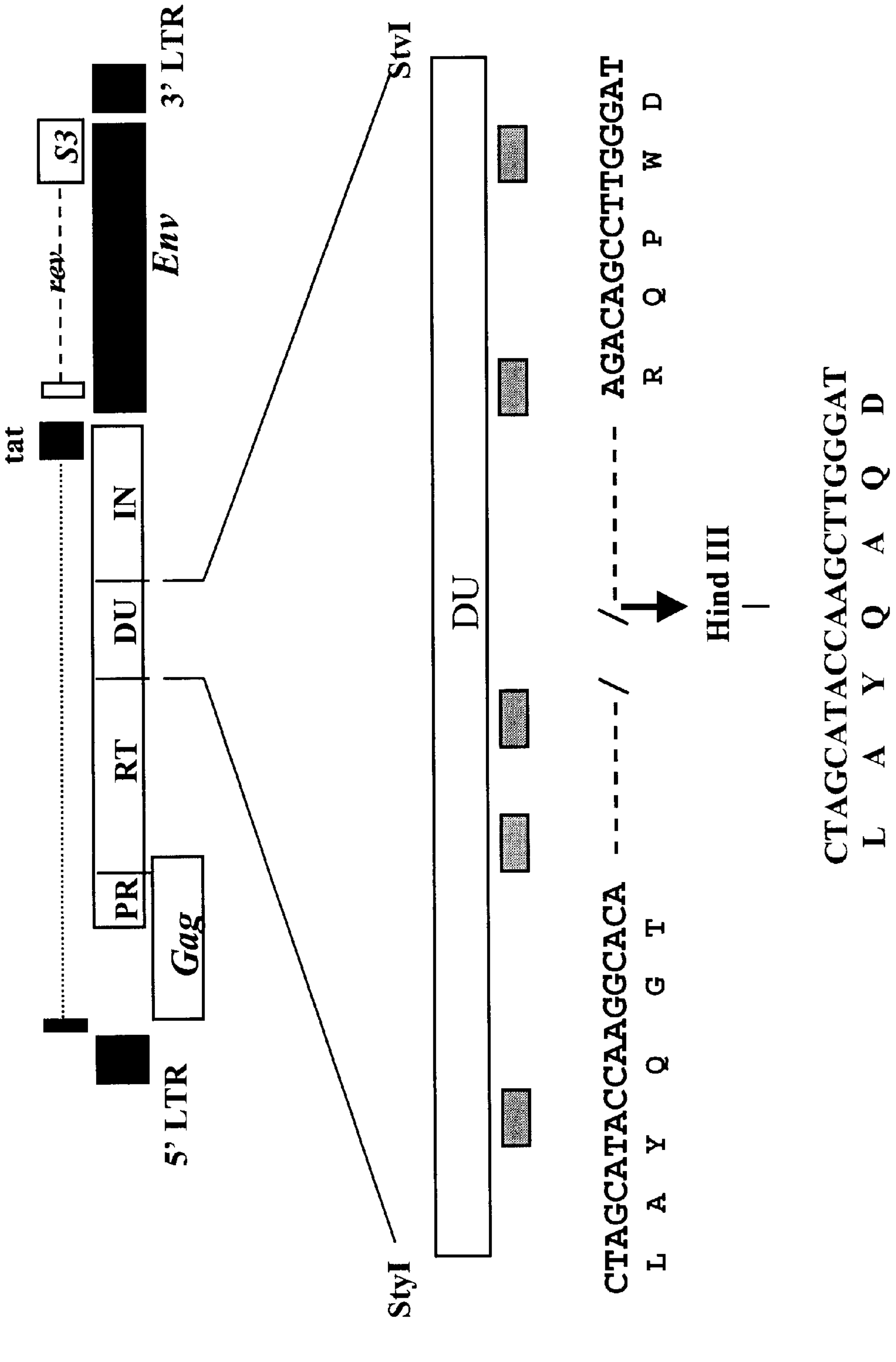

SEQUENCE LISTING

```
<160> NUMBER OF SEQ ID NOS: 10

<210> SEQ ID NO 1
<211> LENGTH: 34
<212> TYPE: DNA
<213> ORGANISM: Gibco BRL

<400> SEQUENCE: 1
```

-continued

```
tttacactag tatactccca tatatatcaa acct                              34


<210> SEQ ID NO 2
<211> LENGTH: 19
<212> TYPE: DNA
<213> ORGANISM: Gibco BRL

<400> SEQUENCE: 2

catgctgttc ttactgtca                                               19


<210> SEQ ID NO 3
<211> LENGTH: 27
<212> TYPE: DNA
<213> ORGANISM: Gibco BRL

<400> SEQUENCE: 3

cctcattgca ctaagcaagg atcagga                                      27


<210> SEQ ID NO 4
<211> LENGTH: 25
<212> TYPE: DNA
<213> ORGANISM: Gibco BRL

<400> SEQUENCE: 4

gatagcttct aataatgtag cagta                                        25


<210> SEQ ID NO 5
<211> LENGTH: 21
<212> TYPE: DNA
<213> ORGANISM: Gibco BRL

<400> SEQUENCE: 5

atatcaaacc ttataacaaa t                                            21


<210> SEQ ID NO 6
<211> LENGTH: 21
<212> TYPE: DNA
<213> ORGANISM: Gibco BRL

<400> SEQUENCE: 6

attatttggt aaaggggtaa c                                            21


<210> SEQ ID NO 7
<211> LENGTH: 27
<212> TYPE: DNA
<213> ORGANISM: Gibco BRL

<400> SEQUENCE: 7

gcgatgctga ccatgttacc cctttac                                      27


<210> SEQ ID NO 8
<211> LENGTH: 27
<212> TYPE: DNA
<213> ORGANISM: Gibco BRL

<400> SEQUENCE: 8

attctacggg gtgatcccag ggggaat                                      27


<210> SEQ ID NO 9
<211> LENGTH: 24
<212> TYPE: DNA
<213> ORGANISM: Gibco BRL

<400> SEQUENCE: 9
```

-continued

```
ccattgtcag ctgtgtttcc tgag                                          24


<210> SEQ ID NO 10
<211> LENGTH: 26
<212> TYPE: DNA
<213> ORGANISM: Gibco BRL

<400> SEQUENCE: 10

ccaaagtatt cctccagtag aacctg                                        26
```

EQUINE INFECTIOUS ANEMIA CHALLENGE MODEL FOR TESTING VACCINES, DIAGNOSTICS AND TREATMENTS

BACKGROUND OF THE INVENTION

1. Field of the Invention

The invention relates to a method for infecting equines with equine infectious anemia (EIA) in order to reproduce a natural infection challenge model comprising administering at least 1 median horse infective dose (MHID) to an equine, preferably on a repeated basis via an intravenous route. The model can be used for testing vaccines for their ability to protect equines from EIA, drugs or other treatments that can be used to treat equines infected with EIA or diagnostic procedures for detection of the EIA status of an equine.

2. Brief Description of the Prior Art

The equine infectious anemia virus is a member of the lentivirus subfamily of retroviruses and causes persistent infection and chronic disease in horses worldwide. As such, it is closely related to human immunodeficiency virus (HIV), simian immunodeficiency virus (SIV) and feline immunodeficiency virus (FIV). As with HIV and SIV, disease caused by EIAV is spread by blood transmission. With EIAV, the blood transmission most often occurs by biting flies and other insects carrying virus particles from one horse to another. The first cycle of disease (clinical episode or first febrile episode) in an infected horse usually occurs within 42 days after transmission of the virus. This first cycle is usually characterized by the acute stage of EIA and manifested by pyrexia, thrombocytopenia, anorexia, depression and high plasma viremia levels. Anemia is not usually detected at this stage. Resolution of this first febrile episode is normally observed after 1 to 5 days and occurs concomitantly with a dramatic drop in the amount of plasma-associated virus. Following the acute stage, some animals may remain clinically normal, while others go on to experience multiple bouts of illness in which severe anemia may accompany pyrexia, thrombocytopenia, edema, and dramatic weight loss, and death. Nucleotide sequence data has revealed a high mutation rate of this lentivirus genome during persistent infection (Payne et al, Virology, 1987: 161, pp 321–331) incorporated herein by reference. It is generally known that multiple isolates from the field demonstrate similar genomic differences indicating that EIAV, as HIV and FIV, undergoes a continuing mutation process within its various hosts. It is generally thought that neutralizing antibodies aid in the selection of new antigenic virus variants (mutations) during persistent infections. In infections with EIAV, serologically distinct variants emerge possibly through immune selection pressure operating on random viral genome mutations. It is proposed that horses that show no further clinical signs of disease have developed a mature immune response that can contain the virus and its immunologically-recognized mutants.

The disease is significant because horses that demonstrate exposure to EIAV via testing for antibodies in the blood (Coggins Test or similar anti-p26 antibody detecting test) are required to be destroyed or strictly quarantined. Because of the Coggins Test and its broad use in the world, especially in testing all performance horses that are transferred into and out of the United States, it is critical that vaccinated equines be able to be differentiated from infected equines.

In testing vaccines, treatments or diagnostics for EIA it is imperative that clinical disease can be reproduced in equids. Previously, Issel et al (J. Virol June 1992, pp 3398–3408) attempted to test vaccines comprising purified env proteins from the equine infectious anemia virus (EIAV) for use as vaccines. The equid model used involved challenge of ponies with 300 median equine infectious doses (MEID) of pathogenic EIAV. There was no protection with heterologous strains of EIAV. In fact, this test demonstrated that these vaccines produced an enhanced disease when the ponies were challenged with a heterologous EIAV strain. Since all the previous work involved use of ponies and use of high challenge doses, there was no information on whether horses could be infected with EIAV, whether horses would develop clinical signs of EIA or whether a dose of 300 MEIDs was too high or too low for horses.

In order to understand how the model in the present invention can be used, it important to understand the genetic organization of EIAV. Therefore, a summary explanation follows.

The genetic organization of EIAV, as with HIV, SIV and FIV contains only three accessory genes (S1, S2 and S3), in addition to the gag, pol and env genes common to all retroviruses. The S1 open reading frame (ORF) encodes the viral Tat protein, a transcription trans activator that acts on the viral long-terminal-repeat (LTR) promoter element to stimulate expression of all viral genes. The S3 ORF encodes a Rev protein, a post-transcriptional activator that acts by interacting with its target RNA sequence, named the Rev-responsive element (RRE), to regulate viral structural gene expression. The S2 gene is located in the pol-env intergenic region immediately following the second exon of Tat and overlapping the amino terminus of the Env protein (see FIGS. 1, 2*a* and 2*b*). It encodes a 65-amino-acid protein with a calculated molecular mass of 7.2 kDa, which is in good agreement with the size of an in vitro translation product. S2 appears to be synthesized in the late phase of the viral replication cycle by ribosomal leaky scanning of a tricistronic mRNA encoding Tat, S2 protein, and Env, respectively. The ORF coding for the S2 protein of EIAV is highly conserved in all published EIAV sequences and contains three potential functional motifs (FIG. 2*a*): GLFG (putative nucleoporin motif), PXXP (putative SH3 domain binding motif) and RRKQETKK (putative nuclear localization sequence). Antibodies to S2 protein can be found in sera from experimentally and naturally infected horses, indicating that S2 is expressed during EIAV replication in vivo. These observations suggest that S2 is likely to perform an important role in the virus life cycle. A discussion of the function of S2 is found in Li et al (J. Virol., October 1998, p 8344–8348), incorporated herein by reference.

A second interesting gene contained within the lentivirus group codes for dUTPase. This enzyme catalyzes the conversion of dUTP to dUMP and $pp_i$. The gene encoding the dUTPase has been mapped within the pol gene for EIAV and FIV. The lentivirus dUTPase gene has been designated DU. Studies with DU deletion mutants (ΔDU) of EIAV and FIV show that this enzyme is not required for replication of the viruses in fetal equine kidney cells or Crandell cells. However, efficient replication of the EIAV or FIV in monocyte/macrophage cells (typical replication host cell) does require DU. The differences indicated have been described in detail in a publication by Lichtenstein et al (J. Virol., May 1995, p 2881–2888), incorporated herein by reference.

Envelope proteins (env) are thought to be required for protection from disease and, perhaps, protection from infection. By protection from disease is meant that a mammal exposed to the virus, does not demonstrate clinical signs (fever, lethargy, anemia, etc.) but does carry particles associated with the viral RNA genome (shortened herein to viral particles) in its blood, said particles being detectable by a reverse transcriptase polymerase chain reaction test (RT-PCR). By protection from infection is meant that a mammal exposed to the virus does not demonstrate clinical signs nor does its blood contain RT-PCR-detectable virus particles as described above. The major envelope proteins of EIAV are gp90 and gp45. These are proposed as the protective antigens of EIAV. By the term protective antigens is meant antigens from EIAV that produce either protection from disease or protection from infection as indicated above.

Since there have been no reports of challenge models in which EIA can be reproduced in horses such that the natural infection is reproduced, there has been no effective method for testing vaccines, treatments or diagnostics.

BRIEF DESCRIPTION OF THE DRAWINGS

FIG. 1 is a schematic diagram of replication competent EIAV including the location of the accessory genes of $EIAV_{UK}$.

FIG. 2*a* is a schematic representation of the EIAV S2 gene and mutant clones derived from EIAVuk.

FIG. 2*b* is a schematic representation of the Wild-type EIAV S2 gene compared with the EIAV.2M/X ($EIAV_{UK}$S2) gene.

FIG. 3*a* is a circular map of biological proviral clone $EIAV_{PR}$.

FIG. 3*b* is a circular map of molecular infectious clone $EIAV_{UK}$.

FIG. 3*c* is a circular map of mutant $EIAV_{UK}$S2.

FIG. 3*d* is a circular map of mutant $EIAV_{PR}$S2.

FIG. 3*e* is a circular map of mutant $EIAV_{UK}$DU S2

FIG. 4 are graphs demonstrating the in vitro replication of EIAV mutant clones.

FIG. 5 is a schematic representation of the DU gene location and construction of EIAVΔDU.

DETAILED DESCRIPTION OF THE INVENTION

Encompassed by the invention is a method for infecting equines with EIAV in order to reproduce a natural infection, Said method comprises injecting said equine with at least one dose of at least one median horse infective dose (MHID) of EIAV by a route that produces clinical disease signs of EIA as well as infection with EIAV. By clinical disease signs or disease is meant that the equine demonstrates the typical pyrexia, thrombocytopenia, depression and, optionally, anorexia. By infection is meant that high levels (>$10^5$ units of RNA as detected by PCR, also noted as EIAV particles) of EIAV are found in the blood or plasma of the inoculated horse.

Routes of inoculation of horses include but are not limited to intravenous, intramuscular, intranasal, subcutaneous, intraperitoneal or combinations thereof. The preferred route of inoculation is intravenous.

The method of reproducing EIA encompasses repeated inoculation of at least one MHID, preferably, 10 MHID to horses using the intravenous route. Preferably, three doses are administered within an interval of 7 days. More preferably, 10 MHIDs of EIAV are administered every other day for a total of 3 doses. This generally produces disease and infection in horses within 40 days post inoculation.

It is contemplated that the EIA equine challenge model described in the present invention can be used to test the efficacy or immunogenicity of vaccines (ability of the vaccine to protect equines from disease and/or infection caused by EIAV). It is also expected that the EIA equine challenge model described in the present invention can be used to test new treatments for lentivirus diseases including but not limited to EIA. Finally, it is contemplated that diagnostic tests for confirmation of EIA in equines can be evaluated using the EIA equine challenge model described herein.

This invention also describes a vaccine for effectively and safely immunizing mammals, especially equids, from disease caused by EIAV, said vaccine being tested for efficacy or immunogenicity using the EIA equine challenge model described herein. The vaccines tested comprised a gene-mutated EIAV wherein said virus lacked the ability to express the mutated gene protein in vivo and wherein said lack of expression can be used to differentiate vaccinated from non-vaccinated or infected mammals. The EIA equine challenge model described herein could be used to evaluate a diagnostic test for differentiation between vaccinated and non-vaccinated equines vaccinated with the EIAV vaccines described herein. Therefore, it is within the scope of this invention that a diagnostic test can be used to differentiate vaccinated equines from non-vaccinated and/or infected equines by measuring the presence or absence of antibodies to the S2 protein, to the DU protein or to both proteins. Also, a PCR-based diagnostic test could be used to detect the presence or absence of the S2 and/or DU genes or gene sequences in the equine and, thus, detect whether an equine had been infected with EIAV or vaccinated with the composition of this invention.

In accord with the invention, it has been found that the S2 antibodies can be detected in horses with EIAV infections by using immunoassays comprising recombinant S2 protein or synthetic S2 peptides as the capture antigen. Additionally, it has been determined that the presence of the type of virus found in a mammal can be differentiated between the vaccine virus and the wild-type virus by use of gene probes (PCR-based). It has also been determined that the S2 gene of EIAV is not required for in vitro replication in a variety of equine cells including but not limited to Fetal Equine Kidney cells (FEK), equine dermal cell lines (ED) or cultured equine monocytes/macrophages. It has further been determined that the S2 deletion mutant replicates in vivo only at very low levels as compared with the wild-type EIAV (Li, et al, January 2000, J. Virol. P. 573–579), incorporated herein by reference. By low levels is meant that the virus produces less than $1\times10^5$ EIAV particles as measured by PCR preferably less than $1\times10^4$. Further, it has been determined that the S2 protein is not a component of purified EIAV particles and that horses immunized with purified EIAV particles do not produce serum antibodies reactive with in vitro synthesized S2 protein or peptides. Therefore, even horses vaccinated with purified EIAV particles can be differentiated from wild-type infected horses. These results indicate that the presence of S2 specific antibody can be used to identify EIAV-infected horses and to distinguish infected horses from those that have been vaccinated with an inactivated whole virus or an attenuated vaccine in which the S2 gene is mutated so as to make it non-functional. Therefore, it is within the scope of this invention that a diagnostic test can be used to differentiate vaccinated equines from non-vaccinated and/or infected equines by measuring the presence or absence of antibodies to the S2 protein, to the DU protein or to both proteins. Such differentiation can be measured by developing an immunoassay, an antibody-detecting assay (e.g., indirect fluorescent antibody, immunodiffusion, agar diffusion, electrophoresis) or a PCR-based assay known to the art. An example of an immunoassay is an enzyme linked immunosorbant assay (ELISA) that detects and/or quantitates antibodies to specific proteins in serum, blood or tissues. ELISA technology could also be used to detect the presence or absence of virus-associated antigens in the blood, serum or tissues. By virus associated antigens is meant the presence or absence of a gene expression product such as the S2 or DU proteins in the case of the S2 or DU genes, respectively. Additionally, PCR-based assays have been used to measure the presence or absence of genes or gene sequences in the blood, serum or tissues of an equine, thus indicating that a horse had been infected or vaccinated, as the case may be. For this particular embodiment, an ELISA would detect the presence of antibodies to the S2 or DU proteins. If antibodies were present in horses that were tested it would indicate that the horse had been infected with EIAV. Horses that had been vaccinated with a gene-mutated EIAV construct containing a non-functional S2 gene would not contain S2 antibodies in their serum. Horses that had been vaccinated with a gene-mutated EIAV construct containing a non-functional DU gene would not contain DU antibodies in their serum. Thus, vaccinated horses could be differentiated from infected horses. The PCR-based assays would be used to detect the presence or absence of gene sequences within the horse. For instance, if a horse had been infected with a wild-type EIAV, it would contain the gene sequence for wild-type S2 or DU. However, equines immunized with vaccines comprising a gene-mutated EIAV, particularly one wherein the S2 or DU genes comprised deletions or specific mutations would not contain the gene sequence for wild-type S2 or DU gene products.

Vaccines tested using the EIA equine challenge model of the present invention have been either inactivated or administered live. Inactivated vaccines of the present invention comprise treatment of the live virus, attenuated virus, purified virus particles or whole virus particles with agents that inactivate the virus such that it cannot replicate in vitro or in vivo. Such agents are selected from the group consisting of formalin, formaldehyde, beta-propriolactone, binary ethyleneimine, ethyleneimine, merthiolate, thimerosal, psoralen and combinations thereof. These agents can be used at concentrations varying from 1 part per billion to 0.5%, depending on the agent. For instance, thimerosal would be used at a concentration of between 1 part per 1,000 and 1 part per billion, preferably between 1 part per 5,000 and 1 part per 100,000. Formalin would be used at a concentration between 0.00001% and 0.5%, preferably between 0.0001% and 0.1%. Ethyleneimine would be used at a concentration between 0.00001M and 0.1M, preferably between 0.0001M and 0.01M. Beta-propiolactone would be used at a concentration similar to that used for ethylenimine.

Vaccines of the present invention may also include adjuvants in order to enhance the immune response. Adjuvants are chemical agents or extracts of microorganisms that induce an enhanced immune response. When accompanied by an antigen, they enhance the immune response produced by the antigen. In the case of EIAV particles, EIAV purified virus particles, EIAV constructs, attenuated EIAV, EIAV (whole virus) or EIAV subunits, adjuvants may be added to enhance the immune response to the vaccine composition to provide improved protection. It is recognized that adjuvants would be used according to the present invention at concentrations varying from 0.1% to 50% v/v, preferably from 1% to 20%. Although any adjuvant will enhance the immune response and can be used with the vaccine compositions of the present invention, it is within the teaching of the present invention that adjuvants selected from the group consisting of polymer-based, oil-based, block copolymer-based, aluminum salt based, organism-based, lipid-based and aqueous-based, surfactants are preferred. Non-limiting examples of surfactants useful as adjuvants include hexadecylamine, octadecylamine, lysolecithin, demethyidioactadecyl ammonium bromide, N,N-dioctadecyl-N'-N-bis (2-hydroxyethylpropane diamine), methoxyhexa-decylglycerol and pluronic polyols and saponin, Quil A. Non-limiting examples of polyanions or polycations include pyran, diethylaminoethyl (DEAE) dextran, dextran sulfate, polybrene, poly IC, polyacrylic acid, carbopol, ethylene maleic acid, aluminum hydroxide, and aluminum phosphate. Non-limiting examples of peptide adjuvants include muramyl dipeptide, dimethylglycine and tuftsin. Non-limiting examples of other types of adjuvants include oil emulsions, immunomodulators (interleukin-1, interleukin-2 and interferons) or combinations of any of the foregoing adjuvants. A number of acrylic acid polymers and copolymers of acrylic acid and methacrylic acid and styrene have adjuvant activity. Polyvinyl Chemical Industries (Wilmington, Mass.) provides such polymers under the trade-name NEOCRYL®, BEOCRYL A640, an aqueous acrylic copolymer with styrene. Other useful NEOCRYL products are 520 and 625, and NEOREZ 966. Ethylene maleic acid, produced from ethylene maleic anhydride is a preferred adjuvant. In order to produce ethylene maleic acid, EMA 31 or EMA 91 (Monsanto Co., St. Louis, Mo.) is prepared in an aqueous solution at a concentration between 0.1 and 10% (w/v), preferably between 0.5 and 5% (w/v). It is used in product at a concentration of 1 to 50% (v/v). More preferably, Carbopol is used as an adjuvant alone or in combination with tweens, spans and oils. Representatives of this type of adjuvant are HAVLOGEN® and SPUR®. These adjuvants are prepared by mixing Carbopol 934P at a concentration between 0.5 and 10% (w/v), preferably between 1 and 5% (w/v), more preferably between 2.0 and 4% (w/v). Added to the Carbopol can be detergents such as Tween 80 and Span 20, and an oil for producing an emulsion. The oils can be cottonseed, peanut, mineral, or any other type known to be safe for use in animals. The concentrations of the oil ranges from 0.000001% to 10% (v/v), preferably from 0.00001% to 5% (v/v), more preferably from 0.0001% to 1% (v/v). Other commercially-available adjuvants useful for this vaccine include but are not limited to POLYGEN™, a polymer-based low molecular weight, non-particulate copolymer which can form cross-linkages in solution to become a high molecular weight gel (MVP Laboratories, Inc., Ralston, Nebr.) or EMULSIGEN™ or EMULSIGEN™ PLUS, both oil-in-water adjuvants provided by MVP Laboratories, Inc. Organism-based adjuvants are those utilizing whole microorganisms or extracts of microorganisms, such as Muramyl Dipeptide, RIBI®, whole Parapox viruses or extracts thereof (also known as Baypamun) and *Corynebacterium acne* extracts. Lipid-based adjuvants include but are not limited to BAY R1005, liposomes and ISCOMS. The most preferred adjuvants of the present invention include HAVLOGEN®, POLYGEN™, BAY R1005, Baypamun and ethylene maleic acid-based. Often, two or more adjuvants can be used to formulate with the EIAV constructs of this invention.

In order to better understand the examples of this invention the following explanation of terminology is provided. The wild-type EIAV is referred to as the Wyoming isolate or EIAVwyo. This virus is termed a primary isolate and it replicates only in equine monocyte-macrophage cell cultures in which the virus is cytopathic for the infected cells by 7–10 days post infection. Thus, EIAVwyo can be produced only in short-term macrophage cultures to obtain infectious virus in cell supernatants or in experimentally infected horses to obtain infectious plasma (Malmquist et al. 1973, Arch. Virol. 42, p 361–370). Either source of the primary isolate EIAVwyo can be used to experimentally infect equids and produce classical EIA disease. To obtain a cell-adapted strain of EIAVwyo that is able to replicate in other cell types, the primary EIAVwyo isolate was serially passaged in equine cells to produce a stock of EIAV virus that could be grown on various fibroblastic cells (Malmquist et al 1973, Arch Virol. 42, p 361–370; Parekh et al. 1980 Virology 107:520–525). The cell-adapted EIAVwyo was then grown in fetal equine kidney cell cultures to produce larger amounts of virus and thus used to prepare stocks of the cell-adapted virus designated $EIAV_{PR}$ (Montelaro et al. 1982 J. Virology 42:1029–1038). Inoculation of ponies with the avirulent $EIAV_{PR}$ resulted in 100% infection but did not produce EIA disease, confirming the attenuated avirulent nature of the $EIAV_{PR}$ Strain (Orrego et al. 1982 Am. J. Vet. Res. 43:1556–1560). To obtain a reference strain of EIAV that could be grown in fibroblastic cells and produce disease in experimentally-infected equids, the $EIAV_{PR}$ strain was serially passaged in ponies and isolated in the context of infectious plasma after the third serial passage (Orrego et al. 1982 Am. J. Vet. Res. 43:1556–1560). The in vivo serial passage restored virulence to the EIAV, but did not cause it to lose its ability to replicate in cells other than equine macrophages. This virus stock in infectious plasma was designated as host-adapted EIAVwyo. Inoculation of ponies with high amounts of host-adapted EIAVwyo induced 100% infection and clinical EIA disease (Payne et al. 1987 Virology 161:321–333). In a subsequent set of experiments, a host-adapted EIAVwyo was grown in fetal equine cell culture in the presence of neutralizing immune serum from a pony to generate antigenic neutralization escape mutants by antibody selection that were then biologically cloned to obtain a more homogeneous genomic population (Rwambo et al., 1990, Arch. Virol. 111:pp 275–280). Subsequent stocks of this biologically cloned reference virus produced in fetal equine kidney cell culture were termed $EIAV_{PV}$ to indicate "pony virulent". Infection of ponies with the biologically cloned $EIAV_{PR}$ resulted in 100% infection and disease (Hammond et al. 1997 J Virology 71:pp 3840–3852). Since lentiviruses like EIAV exist in nature as complex genomic mixtures termed quasispecies, primary isolates (EIAVwyo) and biological clones ($EIAV_{PV}$) contain a variety of genomic species. To obtain genetically homogenous forms of EIAV, infectious molecular clones were derived from the avirulent $EIAV_{PR}$ (e.g., EIAV 19-2) (Payne et al 1994 J. Gen. Virol. 75:425–429) and pathogenic $EIAV_{PV}$ (Cook et al. 1998 J. Virology 72:1383–1393) reference stocks by standard molecular biology cloning procedures. Inoculation of ponies with infectious virus stocks produced from chimeras with EIAVpr and EIAVpv sequences (e.g., $EIAV_{UK}$) were shown to produce disease in experimentally-infected horses. The infectious molecular clone $EIAV_{UK}$ was the first reported pathogenic molecular clone.

FIG. 3*b* displays the circular map of this infectious molecular clone, $EIAV_{UK}$. In order to provide further information for the following examples, FIG. 3*c* displays the circular map of $EIAV_{UK}\Delta S2$, FIG. 3*d* displays the circular map of $EIAV_{PR}\Delta S2$, and FIG. 3*e* displays the circular map of $EIAV_{UK}\Delta DU\Delta S2$.

The invention is further illustrated but is not intended to be limited by the following examples in which all parts and percentages are by weight unless otherwise specified.

EXAMPLE 1

Several different gene-mutated EIAV constructs were prepared according to the methods of Li et al (J. Virol., October 1998, pp 8334–8348) which are incorporated herein by reference. The basic S2 gene mutations were designed so as not to disrupt the second exon of Tat 10 base pairs (bp) upstream from the S2 initiation sequence, the envelope initiator codon just 23 bp downstream from the S2 start codon sequence, or the putative Rev-response element (RRE) sequences that have been mapped to both the 5' and 3' ends of the env gene. A panel of clones with substitutions that introduce one or more premature stop codons (EIAV.2M/X and EIAV.G5/s) or with a deletion of the first 5 nucleotides of the S2 gene to shift the S2 ORF (EIAVΔS2) were produced. These are schematically diagrammed in FIGS. 2*a* and 2*b*. The EIAV proviral DNA is shown at the top; the complete deduced amino acid sequence of the putative S2 protein is shown in single letter amino acid code at the bottom. Stop codons (indicated by arrows) were introduced into various positions in the EIAV S2 gene to generate the specific mutant virus strains. As would be recognized, all of the constructs would be considered to be non-functional for S2 and will be referred to herein as ΔS2.

S2 mutant constructs were generated using the PCR-Ligation-PCR (PLP) strategy as previously described (Puffer, et. al., 1997 and Li, et. al., 1998). $EIAV_{UK}$ plasmid DNA was used as the template to perform all PCR reactions for generating S2 mutations except for $EIAV_{UK}$.2M/X.

EIAV.G5/s was generated using $EIAV_{UK}$ as the template by PCR with Pfu polymerase (Stratagene) by using mutagenic downstream primer mspe3-5' (SEQ ID NO: 1) with upstream primer s2pst (SEQ ID NO: 2). A second flanking fragment was amplified using mutagenic upstream primers mspe5'-3' (SEQ ID NO: 3) and s2sph (SEQ ID NO: 4).

$EIAV_{UK}\Delta S2$ was similarly generated using $EIAV_{UK}$ as the template by PCR with Pfu polymerase (Stratagene) by using downstream primer S2min/35rev (SEQ ID NO: 5) and upstream primer s2pst (SEQ ID NO: 2). A second flanking fragment was amplified using mutagenic upstream primer S2min/53for (SEQ ID NO: 6) and s2sph (SEQ ID NO: 4).

Each of these corresponding two adjacent PCR fragments were gel purified, phosphorylated using T4 polynucleotide kinase (Gibco BRL), and ligated by using T4 DNA ligase (Gibco BRL). After inactivation at 65° C. for 15 minutes, the ligation reaction was used for a subsequent amplification using upstream primer s2pst (SEQ ID NO: 2) and downstream primer s2sph (SEQ ID No: 4). This product was gel purified, digested with NcoI and Bpu1102l, and then ligated into the NcoI and Bpyu1102l sites of $EIAV_{UK}$.

$EIAV_{UK}$.2M/X, which has its sequence compared with that of $EIAV_{UK}$ in FIG. 2*b,* was generated using the $EIAV_{UK}$G5/s plasmid DNA as a template with downstream primer 2M35/RE (SEQ ID NO: 7) and upstream primer s2pst (SEQ ID NO: 2). A second flanking fragment was amplified using mutagenic upstream primer 2M53/For (SEQ ID NO: 8) and downstream primer s2sph (SEQ ID NO: 4). The final cloning procedure was as described above.

For simplification and because all of the EIAV constructs described are non-functional for S2 as demonstrated in tissue culture growth studies (as described in EXAMPLE 2), these EIAV constructs have been redesignated $EIAV_{UK}\Delta S2$.

Standard PCR conditions used for the above-described reactions included, one cycle of denaturation at 95° C. for 5 min., followed by 35 cycles of denaturation at 95° C. for 30 seconds, 60° C. for 30 seconds and 72° C. for 30 seconds. The PCR reactions were set up using the following components:

10 μL 10×NEB Thermophilic buffer 1.0 Lμ 10 mM deoxynucleotide triphosphates dNTPs 1.0 μM forward primer (upstream primer)

1.0 μM reverse primer (downstream primer)

10 ng template DNA x μL double distilled water ($ddH_2O$) (q.s. to 100 μL volume)

A 10 μL aliquot was run on an 1.0% agarose gel to make sure the correct size product was amplified. The PCR products were then gel isolated and purified with a Qiaex II gel extraction Kit (150)(Qiagen, Cat. # 20021). The Qiaex II protocol is presented below:

1. Cut band from gel and place in a 1.5 mL eppendorf tube
2. Estimate the volume of agarose gel slice, add 3 volumes of buffer QX1, if the fragment is <4 kb, and an additional 2 volumes of $ddH_2O$ if the fragment is >4 kb.
3. Vortex the Qiaex II beads and add 10 μL to the agarose slice suspension
4. Mix well, incubate at 50° C. for 5–10 minutes, mixing the tube several times during the incubation period.
5. Centrifuge the sample for 30 seconds and carefully remove the supernatant with a pipette followed by washing the pellet once with 500 μL of buffer Q×1.
6. Wash the pellet twice with 500 μL of buffer PE, and air dry pellet 15–30 minutes at room temperature.
7. Resuspend the pellet in 20 μL of $ddH_2O$, incubate at 55° C. for 10 min., spin at full speed for 30 seconds.
8. Pull off supernatant and save to a clean eppendorf tube. Measure the OD at 260 nm for the concentration of the recovered fragment on an agarose gel.
9. Add $ddH_2O$ as needed to resuspend the pellet.

The two adjacent PCR fragments were individually phosphorylated in the following reaction mixture by using T4 polynucleotide kinase (NEB) prior to ligation. The phosphorylation reaction was set up as follows:

2.0 μL 10×T4 polynucleotide kinase (PNK) buffer (NEB)

2.0 μL 10 mM ATP (NEB)

1.0 μL T4 PNK (NEB)

15 μL gel purified DNA of each of these two adjacent PCR fragments

The reaction was incubated at 37° C. for 1 hour. Following inactivation at 65° C. for 10 min. the adjacently phosphorylated PCR fragments were then ligated together by using T4 DNA ligase (NEB) under the following conditions:

1.0 μL 10×T4 DNA ligase buffer (NEB)

X μL (50–100 ng) of each of two adjacent PCR fragments 1.0 μL T4 DNA ligase (NEB)

X μL $ddH_2O$ (q.s. to 10 μL total volume)

After overnight incubation at 16° C. the ligation reaction product was used in a second round PCR reaction to amplify the full-length PCR fragment spanning these two adjacent PCR products. The second round PCR reaction was performed as previously described (see below) with the exception that only upstream primer s2pst (SEQ ID NO: 2) and downstream primer s2sph (SEQ ID NO: 4) were used. Again, a 10 μL aliquot was run on an agarose gel to make sure the correct product was amplified. The full-length PCR fragments were then gel isolated and purified using the Qiaex II kit (see above). The purified full-length PCR fragment, together with $EIAV_{UK}$, were then cut with Ncol (Gibco BRL) and Bpu1 1021 (Gibco BRL) under the following conditions:

2.0 μL 10×React2 buffer (Gibco BRL)

1.0 μL Ncol (Gibco BRL)

1.0 μL Bpu1 1021

X μL full length PCR product (1.0 μg) or $EIAV_{UK}$ (500 ng)

X μL $ddH_2O$ (q.s. to 20 μL total volume)

The above restriction enzyme digestion mixture was incubated at 37° C. for 2 hours. Digested DNA fragments from the full-length PCR product and the $EIAV_{UK}$ plasmid were individually gel isolated and purified using a Qiaex II kit as described above. The digested vector $EIAV_{UK}$ and full length PCR fragment were ligated using T4 DNA ligase using the following procedure:

1.0 μL 10×T4 DNA ligase buffer (NEB)

X μL (25–50 ng) digested $EIAV_{UK}$

X μL (200–400 ng) digested full length PCR fragment 1.0 μL T4 DNA ligase (NEB)

X μL $ddH_2O$ (q.s. to 10 L total volume)

The ligation reaction was incubated at 16° C. overnight and the ligated products were transformed into *Escherichia coli* DH5α (Gibco BRL) by heat shock as described below:

1. Thaw 100 μL of DH5α competent cells and incubate on ice
2. Add 1 μL of ligation mixture to cells, mix gently, and incubate on ice for 30 minutes
3. Heat pulse the tube in a 42° C. bath for 45 seconds and incubate on ice for 2 minutes.
4. Add 0.9 mL SOC broth (2% bactotryptone, 0.5% yeast extract, 10 mM NaCl, 2.5 mM KCl, 10 mM $MgCl_2$, 10 mM $MgSO_4$ and 20 mM glucose, pH 7.0) and incubate the tubes at 37° C. for 1 hour while shaking at 222 rpm.
5. Plate 150 μL of the transformation mixture onto LB-ampicillin (100 μg/mL) plates and incubate at 37° C. overnight.

The proviral clones ($EIAV_{UK}$.2M/X, $EIAV_{UK}$G5/s and $EIAV_{UK}$deltaS2) were then screened by automatically sequencing using a Taq Dye Deoxy Terminator Cycle Sequencer Kit (Applied Biosystems) individually using an internal sense primer S40 (SEQ ID NO: 11) and an internal antisense primer S15 (SEQ ID NO: 12). Following the verification for the mutations in the S2 gene by sequencing, the proviral DNA clones were used for various future studies.

The generation of $EIAV_{UK}\Delta DU\Delta S2$ was based on the modification of the previously studied $EIAV_{PR}\Delta DU$ virus in which the deoxyuridine-triphosphatase (dUTPase or DU) gene segment was deleted by removing a 330-bp Styl restriction fragment (Lichtenstein, et al., 1995). $EIAV_{UK}\Delta DU\Delta S2$ was generated by subcloning into the full-length $EIAV_{UK}\Delta S2$ proviral backbone of a Sstl-Ncol fragment of $EIAV_{PR}\Delta DU$, which contained a 330-bp deletion in the DU gene.

$EIAV_{PR}\Delta S2$ was created by subcloning into the full-length $EIAV_{PR}$ proviral backbone of a Ncol-Bpul1021 fragment of $EIAV_{UK}\Delta S2$, which contained a S2 gene mutation. All of the various constructs discussed above contain a non-functional S2 gene and could be used in vaccines for immunizing horses against diseases caused by EIAV. The constructs are compared with the wild-type EIAV in FIGS.

1 and 2. FIGS. 3*d* and 3*e* represent the circular maps of $EIAV_{PR}\Delta S2$ and $EIAV_{UK}\Delta DU\Delta S2$.

It is expected that each of the gene-mutated EIAV constructs can be used to prepare either live attenuated or inactivated vaccines for safe and effective immunization of horses from disease caused by EIAV and can be used to differentiate vaccinated horses from infected horses. As indicated previously, it is recognized that inactivation would be produced by adding an appropriate amount of any of the inactivating agents listed previously or others known in the art to be acceptable to lentiviruses. An appropriate amount means the lowest concentration of inactivating agent necessary to inactivate all of the virus particles without damaging the protective antigens (immunogens).

EXAMPLE 2

In order to demonstrate that the gene-mutated EIAV constructs from Example 1 could replicate in large-scale, a tissue culture growth study was conducted. One microgram of proviral clone DNA from each of the constructs was used to transfect an ED cell line. The ED cell line (ATCC CRL 6288) was grown in 6 well tissue culture plates seeded with between 2 and $4\times10^5$ ED cells per well in 2 mL of the complete growth Minimum Essential Media with Earles salts (EMEM) plus 10% fetal calf serum, 100 units/mL of penicillin, 100 $\mu$g/mL of streptomycin (Gibco BRL 15140-122) and 2 mm L-glutamine (Gibco BRL 25030-081). The plates were incubated at 37° C. in a $CO_2$ incubator approximately 16 to 24 hours until the cells were between 50 and 80% confluent. For each transfection, 1 $\mu$g of DNA was diluted into 100 $\mu$L of OPTI-MEM I Reduced Serum Medium (Gibco BRL 18324-012) and 10 $\mu$L of Lipofectamine reagent (Gibco BRL 18324-012) was added to 100 $\mu$L of OPTI-MEM I Reduced Serum Medium (OPTI-MEM RSM). The two solutions were mixed gently and incubated at room temperature for 30 minutes to allow the DNA-liposome complexes to form. During this time, the ED cell cultures were rinsed once with 2 mL of OPTIMEM I RSM. For each transfection, 0.8 mL of OPTI-MEM I RSM was added to the tube containing the DNA-liposome complexes, the tube was mixed gently and the contents were overlayed onto the rinsed cells. No antibiotics were added during transfection. The DNA-liposome/tissue cultures were incubated for 5 hours at 37° C. in a $CO_2$ incubator. Following incubation, 1 mL of complete growth MEM containing twice the normal concentration of serum was added to the cell culture without removing the transfection mixture. Twenty four hours following the start of transfection the medium was replaced with fresh complete growth medium (EMEM). Starting at 48 to 72 hours post transfection, aliquots of the tissue culture supernatants were taken at periodic intervals and analyzed by using a standard reverse transcriptase (RT) assay as a measure of virus production. Supernatants resulting in RT activity were titrated in an infectivity assay based on cell-ELISA readings as described by Lichtenstein et al, 1995. After titer determination, aliquots of each of the virus construct stocks were frozen at −80° C. for further evaluation and use. All of the constructs replicated well in both ED cells and in MDM cells producing RT levels of at least 10,000 CPM/10 $\mu$L which was the normal level of RT activity observed in wild-type $EIAV_{UK}$ (See FIG. 4). Further passaging of the transfected cells in larger vessels was accomplished by use of the same techniques as described and serves as the basis for indicating that the constructs prepared in Example 1 could be produced in large-scale and, therefore, could be used to prepare vaccines.

The tissue culture grown virus construct stocks were molecularly characterized by extracting viral RNA and conducting RT-PCR analyses of the DU and S2 genes using 20% glycerol cushion purified virus construct particles. These sequence analyses confirmed the DU and/or S2 gene mutation in their corresponding virus constructs. The RT-PCR technique was also employed to identify recombinant virus construct stocks. Wild-type $EIAV_{UK}$ generated a RT-PCR product of 592 base pairs (bp). In contrast, virus constructs containing the DU deletion ($EIAV_{UK}\Delta DU\Delta S2$) resulted in a RT-PCR fragment of 262 bp. S2 gene mutant virus constructs identified as $EIAV_{UK}\Delta DU\Delta S2$, $EIAV_{UK}\Delta S2$ and $EIAV_{PR}\Delta S2$ were also analyzed by the RT-PCR technique. While creating the S2 mutation, a SpeI restriction digestion site was created. RT-PCR and restriction digestion analyses of each of $EIAV_{UK}\Delta S2$, $EIAV_{UK}\Delta DU\Delta S2$, $EIAV_{PR}\Delta S2$ and $EIAV_{UK}$ virus stocks demonstrated that $EIAV_{UK}$ wild-type virus generated a 539 bp RT-PCR fragment that was resistant to digestion by SpeI. Each of the above-listed S2 virus constructs was susceptible to digestion by SpeI, resulting in cleavage of the 539 bp RT-PCR product into 347 and 192 bp fragments.

EXAMPLE 3

Natural infection with EIA results from insects, mostly biting flies, taking a blood meal while biting an infected animal and transmitting blood and virus to a susceptible equid during a subsequent bite. In previous studies ponies received high levels of EIAV challenge (approximately 300 MEIDs). After such a high challenge, ponies demonstrated clinical signs of disease as well as infection noted by detecting high levels of EIAV particles in the blood by PCR. The intent of this experiment was to determine whether a dose as high as 300 MEIDs was required for reproduction of natural infection in horses. Therefore, a natural infection challenge model for equines that would more closely represent the natural situation was needed. Such a model was developed for use in horses rather than ponies. $EIAV_{PV}$ was used as the challenge virus. Horses were pretested and challenged as follows. The stock virus, grown in tissue culture as described in Example 2, was serially diluted in 10 fold increments using MEM. This stock virus was administered IV in three doses over a 7 day period of time. Each dose varied from 316 to 0.0316 $TCID_{50}$ in a 1.0 mL volume, depending on the group. There were 2 horses per group. The calculated amounts of virus per dose administered to each group was 316, 31.6, 3.16, 0.316 and 0.0316. Following challenge, all horses were observed for a period of at least 60 days. Clinical signs of EIA were apparent within 23 to 40 days, depending on the challenge dose received. Concurrent with the initial EIA-related fever was a rapid decline in quantity of platelets circulating in the blood (thrombocytopenia), anorexia, visible weight loss and even ataxia. Table 1 shows the results of this challenge titration.

TABLE 1

EIAV$_{PV}$ Multiple Low Dose Challenge

| Dose Est. $TCID_{50}$/mL* | Horse Number | Seroconversion (dpc) by CELISA or AGID | Day of First Fever | Clinical Signs |
|---|---|---|---|---|
| 316 | 541 | 38 | None | None |
| 31.6 | 640 | 38 | None | None |
| | 737 | 28 | 25 | Two fever episodes, anorexia, visible weight loss |
| 3.16 | 736 | 28 | 39 | Single day of fever |
| | 661 | 28 | 23 | Prolonged fever, anorexia, dramatic weight loss, ataxia, thrombocytopenia |
| 0.316 | 744 | 28 | 24 | Two days of fever |
| | 745 | 30 | 30 | Two fever episodes, anorexia, ataxia, thrombocytopenia |
| 0.0316 | 96-05 | N/A | None | None |

dpc = Days post challenge
*estimated $TCID_{50}$/mL

The data in Table 1 demonstrate that horses were highly susceptible to EIA infection. In fact, it was surprising that they were significantly more susceptible than ponies previously infected with the same EIAV challenge. The data in Table 1 demonstrate that a single virus particle as measured by tissue culture infective dose$_{50}$ (TCID50) produced typical infection and clinical disease in horses when administered as a multiple low dose challenge. They also indicate that as little as 1 $TCID_{50}$ of EIAV is approximately equivalent to 10 median horse infective doses (MHID). Therefore, a new challenge model has been developed that mimics the natural infection with EIAV. It was decided that 1 $TCID_{50}$ is effective in producing clinical disease and would insure that each horse would receive at least 10 MHID per inoculation.

EXAMPLE 4

A vaccination/challenge study was conducted with horses using the multiple low dose challenge developed and described in Example 3. This study was conducted in order to demonstrate that this model could be used to evaluate vaccines for protection of equines from EIAV. A vaccine was prepared using proviral clone EIAV$_{UK}$ΔS2. The EIAV$_{UK}$ΔS2 virus construct was grown in primary fetal equine kidney cells (FEK), filtered through a 0.45$\mu$ filter and frozen in aliquots at −80° C. The titers of these virus construct stocks were $10^6$ infectious center doses (ICD) per mL, as measured by using an EIAV infectious center assay in FEK cells (Lichtenstein, et al, 1995), incorporated herein by reference. For these studies, the EIAV$_{UK}$ΔS2 could have been inactivated, preferably, by using agents such as formalin or binary ethylenimine. Additionally, the virus construct could have been adjuvanted with any of several adjuvants, preferably with a Carbopol-based, polymer-based or lipid-based adjuvant. However, for this experiment, the EIAV$_{UK}$ΔS2 was used without inactivation or adjuvanting so as to determine whether it would replicate in vivo as well as whether it replicated in vitro. Thus, this example describes the use of an attenuated live vaccine comprising EIAV$_{UK}$ΔS2 to protect horses against an intravenous multiple low dose challenge with pathogenic EIAV$_{PV}$, a heterologous EIAV. Six horses were vaccinated with 1.0 mL of the virus construct. One horse was left unvaccinated to serve as a Control horse. In the multiple low dose challenge, each horse received three intravenous inoculations of 10 MHID of EIAV$_{PV}$ at two-day intervals. After challenge, the horses were monitored for clinical signs of EIA for about 3 months post challenge. All horses were clinically monitored and maintained in isolation as described by Hammond, et al. (Virology vol: 254, p 37–49). Rectal temperatures and clinical status were recorded daily. Samples of serum, plasma and whole blood were collected from each pony at predetermined intervals. Plasma samples were stored at −80° C. until further processed for semi-quantitative viral RNA analyses or identification of the presence of wild-type challenge virus, and serum samples were stored similarly until testing for quantitative and qualitative serological assays could be performed. Whole blood samples were appropriately fractionated for enumeration of platelets or experimentation with PBMCs. Results of the horse challenge are shown in Table 2.

TABLE 2

Summary of Results of Horse Vaccination/Challenge Study

| Group | Horse No. | Febrile Episode Post Challenge | Abnormal Blood Platelet Count Post Challenge | Protection from Disease | PCR Detection of Challenge strain EIAV$_{PR}$ | Protection From Infection |
|---|---|---|---|---|---|---|
| EIAV$_{UK}$ΔS2 | 60 | NONE | NONE | Yes | Negative | YES |
| | 971 | NONE | NONE | Yes | Negative | YES |
| | 615 | NONE | NONE | Yes | Negative | YES |
| | 9791 | NONE | NONE | Yes | Negative | YES |
| | 9809 | NONE | NONE | Yes | Negative | YES |
| | 9812 | NONE | NONE | Yes | Negative | YES |
| CONTROL | 880 | YES | YES | No | Positive | NO |

These data indicate that the multiple low dose horse challenge model is acceptable for use in testing an EIAV vaccine to evaluate whether the vaccine was efficacious in protecting horses from both disease and infection produced by EIAV. Additionally, these data demonstrated that an EIAV vaccine prepared from $EIAV_{UK}\Delta S2$ protected horses from both clinical disease and infection. Additionally, equines vaccinated with the attenuated $EIAV_{UK}\Delta S2$ construct can be differentiated from infected equines based on the lack of antibody to the S2 protein in vaccinated animals. Such lack of antibody can be determined by any immunological assay known to the art that would demonstrate the presence of S2 antibodies in the blood or serum of infected ponies or horses and the lack of such antibodies in vaccinated ponies or horses. Alternatively, a PCR-based assay known to the art, could be used to detect the presence of the S2 gene sequence in infected horses as compared to the lack of this gene sequence in vaccinated horses.

This horse experiment demonstrates that the multiple low dose challenge model is effective in both reproducing EIA and in demonstrating that horses can be protected from by a vaccine prepared according to the present invention. It is expected that this multiple low dose challenge model can also be used to test drugs for their effectiveness against lentivirus diseases including but not limited to EIAV, HIV, FIV, BIV and SIV.

EXAMPLE 5

The multiple low dose EIA equine challenge model was used to evaluate two additional live attenuated vaccines. These vaccines were also prepared from the EIAV constructs designated $EIAV_{UK}\Delta DU\Delta S2$ and $EIAV_{PR}\Delta S2$ according to the methods described in EXAMPLE 3. Two groups of horses were each inoculated intramuscularly two times (at monthly intervals) with the respective attenuated vaccine. Each vaccine contained approximately $10^5$ infectious-center doses (ICD) in a 1.0 mL dose. Inoculated horses were monitored daily for any clinical signs of EIA post vaccination. Blood samples were taken at weekly intervals for evaluation of vaccine virus replication and for EIA-specific immune responses. At 6 months post vaccination, all 16 vaccinated horses and 2 non-vaccinated control horses were challenged with a multiple low dose challenge with $EIAV_{PV}$ pathogenic virus stock as described previously. The multiple low dose challenge involved inoculating each horse three times with 10 MHID at two-day intervals. The horses were monitored for clinical signs of EIA, for seroconversion in commercial diagnostic assays for p26 and for infection with the challenge virus using RT-PCR for about 3 months post challenge as in Example 4. Table 3 summarizes the results of this study.

Seven of eight (88%) of the $EIAV_{UK}\Delta DU\Delta S2$ vaccinated horses remained asymptomatic post challenge, while six of eight (75%) of the $EIAV_{PR}\Delta S2$ vaccinates were protected from disease post challenge. These clinical data indicate that the vaccines were effective in preventing disease post challenge exposure to a pathogenic $EIAV_{PV}$. However, these vaccines were not as effective as the vaccine tested in Example 4. It is proposed that the reduced protection results from these constructs either being prepared from an avirulent clone of EIA ($EIAV_{PR}$) or a double deletion mutant of the virulent parent clone ($EIAV_{UK}\Delta DU\Delta S2$). It is proposed that addition of an adjuvant to the vaccines of this example would improve their immunogenicity (ability to protect horses from disease) and produce a vaccine that is more protective for disease caused by EIA virus.

Surprisingly, not all of the vaccinated horses seroconverted to p26 as measured by testing for positive antibody status using the Coggins Test. This indicates that a normal p26 assay could be run on vaccinated horses. In order to use this vaccine for commercial purposes, any vaccinated equines that were found to be Coggins Test positive could be confirmed with a test for antibodies for the S2 expression product. If S2 antibodies were present, it would be confirmed that the horses had been infected with a field strain of EIAV and not the EIAV vaccine of the present invention.

It is apparent that the multiple low dose challenge horse model could be used to demonstrate that a weak vaccine was less efficacious that a strong vaccine (compare results of Examples 4 and 5). It can be used to determine whether a vaccine for effectively and safely immunizing equines from disease caused by EIAV can be produced and that vaccinated equines can be differentiated from infected equines using the standard Coggins test for anitbodies to p26 in addition to a test for antibodies to S2 protein or detection of a gene sequence associated with the S2 gene. Antibodies to both proteins as well as the S2 gene sequence are absent in vaccinated and uninfected equines but present in infected equines. Additionally, the absence of antibodies to the DU protein and/or the DU gene sequence can serve as a differential diagnostic test for equids vaccinated with the $EIAV_{UK}\Delta DU\Delta S2$.

It is expected that the attenuated vaccines described in this example were more attenuated than desired. In order to increase their immunogenicity (ability to protect from disease and infection) an adjuvant can be added to the attenuated vaccine or the attenuated viruses can be inactivated as described previously, adjuvanted and administered as repeat doses (2 to 3) for the vaccination series. It is expected that such a modification would protect completely from disease and infection.

TABLE 3

Summary of Attenuated EIAV Vaccine Trial

| Group | Horse | Febrile Episode | RNA $>10^5$ | $EIAV_{PV}$ Positive | P26 ANTIBODY Positive |
|---|---|---|---|---|---|
| $EIAV_{PR}\Delta S2$ | 811 | X | | X | X |
| | 9705 | | | X | X |
| | 9704 | | | X | |
| | 9717 | | | X | X |
| | 9615 | X | X | X | X |
| | 9613 | | X | X | X |
| | 9716 | | | X | X |
| | 9712 | | | X | X |
| $EIAV_{UK}\Delta DU\Delta S2$ | 9708 | | | X | X |
| | 9706 | | | X | X |
| | 673 | | X | X | X |
| | 677 | | | | X |
| | 9711 | | | | X |
| | 666 | X | X | X | X |
| | 711 | | | | |
| | 699 | | | | |
| Control | 9714 | X | X | X | X |
| | 9720 | X | X | X | X |

EXAMPLE 6

In order to determine whether a vaccine comprising only a DU gene-mutated EIAV would be safe and effective in equines, a DU gene-mutated EIAV construct was prepared and tested in the multiple low dose equine vaccination/challenge model for EIAV as described in Examples 4 and 5. The DU coding region of EIAV is located within the pol open reading frame, positioned between the RT and integrase (IN) genes (See FIG. 5). It specifically codes for a dUTPase, an enzyme to convert dUTP to dUMP+$pp_1$. The predicted amino acid sequence of the EIAV DU protein shows a high degree of homology to the dUTPases of other nonprimate lentiviruses and to the human, yeast and *E. coli* enzymes as well. Five conserved amino acid motifs present in all known dUTPase proteins have been recognized and at least one of these motifs has been suggested to be functionally important. Motif 3 contains a highly conserved tyrosine residue, which has been suggested to be involved in catalysis. To construct an EIAV mutant that would be deficient in dUTPase activity, a Styl restriction fragment containing 80% of the DU coding sequence, including four of the five conserved amino acid motifs, was deleted from the provirus clone $EIAV_{PR}$. The deletion left intact the pol open reading frame and both protease-processing sites present on either side of the DU gene. More specifically, to construct the $EIAV_{PR}\Delta DU$ that is deficient in dUTPase acitivty, a 330 bp restriction fragment from a Kpnl-Pstl pol subclone of the proviral clone $EIAV_{PR}$ was deleted. This deleted segment was then subcloned back into a full-length provirus backbone as an Sstl-Ncol fragment to create the mutant provirus clone $EIAV_{PR}\Delta DU$ (see FIG. 5). FIG. 5 shows the genomic organization of EIAV and the location of the DU gene. The position of the two StyI sites used to create the deletion are also shown. The stippled bar represents the approximate positions of five conserved amino acid motifs present in all known DUTPase genes. Nucleotide and amino acid sequences of DU flanking the two Styl sites are shown at the bottom. The leucine residue is the first amino acid of matrue DU protein. A pol cubclone containing the DU gene was digested with Styl, and the resulting 5' termini were filled in with T4 DNApolymerase and ligated to generate the sequence shown by the arrow. The deleted ~gene was then inserted back into a full-length proviral clone.

The mutant produced as described, was tested for its ability to replicate in vitro, a requirement for large-scale vaccine production. FEK cells and the ED cell line were transfected with the $EIAV_{PR}\Delta DU$ as described previously in EXAMPLE 2. It was determined that the RT activity was equal to that of wild-type $EIAV_{UK}$. However, when equine macrophage cultures were transfected with this construct at a multiplicity of infection (MOI) of 0.01, very little replication (as measured by RT activity) was noted. This suggests that such a construct would replicate poorly if at all in horses. The tissue culture grown proviral construct was confirmed to be $EIAV_{PR}\Delta DU$ by RT-PCR. These experiments determined that $EIAV_{PR}\Delta DU$ could be produced in vitro in large scale in either FEK or ED cells.

In order to determine whether a vaccine could be prepared and whether such a vaccine would protect horses from disease and/or infection, the ED cell line was transfected and a large quantity of $EIAV_{PR}\Delta DU$ was produced. In this study, the proviral construct was inactivated by addition of 0.1% formalin and adjuvanted with a polymer-based adjuvant, specifically with a Carbopol-based adjuvant designated HAVLOGEN®. Two vaccines were formulated. One contained 50 μg/dose (1.0 mL) while the second contained 10 μg/dose. Each of three horses received 3 doses of 50 μg/dose vaccine and each of three horses received 3 doses of 10 μg/dose vaccine. The interval between vaccinations was one month. Three additional horses were left unvaccinated and served as negative controls. Nine weeks post final vaccination, all horses were challenged with a multiple low dose challenge using $EIAV_{PV}$, a heterologous strain. This constituted administering 10 $HID_5$, three times over a 7 day period (days 0, 2 and 5). Horses were monitored for temperature, platelet count, plasma viremia and seroconversion for 7 weeks post challenge. Results of this vaccination/challenge study are shown in Table 4.

TABLE 4

Summary of Results of the Vaccination/Challenge Study using an inactivated, Adjuvanted DU gene-mutated EIAV Vaccine

| Group | Horse | Febrile Episode | RNA $>10^5$ | $EIAV_{UK}$ Positive | P26 ANTIBODY Positive |
|---|---|---|---|---|---|
| $EIAV_{PR}\Delta DU$ 50 μg/dose | | | | | |
| | 710 | None | Neg | Neg | X |
| | 682 | None | Neg | Neg | X |
| | 95-03 | None | Neg | Neg | X |
| $EIAV_{PR}\Delta DU$ 10 μg/dose | | | | | |
| | 787 | X | X | X | X |
| | 785 | X | X | X | X |
| | 724 | None | Neg | Neg | Neg |
| Controls | | | | | |
| | 96-08 | X | X | X | X |
| | 827 | X | X | X | X |
| | 746 | X | X | X | X |

It is noted from Table 4 that all three horses receiving a 50 μg/dose of inactivated, adjuvanted vaccine were protected from both disease and infection. These horses demonstrated no clinical signs of disease and did not demonstrate the presence of challenge virus (viremia) as measured by RT-PCR. Even a dose of only 10 μg was able to protect 1 of 3 horses from both disease and infection. All control horses demonstrated both disease and infection typical of full-blown EIA. This is an extraordinary result, especially since the challenge virus that was administered was heterologous, not homologous to the vaccine constructs. These data prove that the teachings of the present invention can be used to prepare and evaluate efficacy of a completely protective vaccine. It also proves that inactivation and adjuvanting do not decrease the immunogenicity of the EIAV vaccines of the present invention.

Although the invention has been described in detail in the foregoing, for the purpose of illustration it is to be understood that such detail is solely for that purpose and that variations can be made therein by those skilled in the art without departing from the spirit and scope of the invention except as it may be limited by the claims.

What is claimed is:

1. A method for infecting an equine in order to produce a model that mimics natural infection comprising administering between about 1 and about 10 median equine infective doses in multiple low dose challenge of an EIAV to equines via a route selected from the group consisting of intravenous, intramuscular, intranasal, intraperitoneal, subcutaneous and a combination thereof.

2. The method of claim 1 wherein said EIAV is an infectious biological clone.

3. The method of claim 1 wherein said EIAV is an infectious molecular clone.

4. The method of claim 2 wherein said infectious biological clone selected from the group consisting of $EIAV_{WYO}$, $EIAV_{PV}$ and $EIAV_{PR}$.

5. The method of claim 3 wherein said infectious molecular clone is a wild type.

6. The method of claim 1 wherein said administration is used to evaluate immunogenicity of an EIA vaccine.

7. The method of claim 1 wherein said administration is used to evaluate treatment regiments for EIA infection and/or disease.

8. The method of claim 1 wherein said equine is selected from the group consisting of horse, mule, donkey, ponies, and the like.

9. The method of claim 1 wherein the administration is repeated.

10. The method of claim 1 wherein three doses are administered within an interval of seven days.

11. The method of claim 1 wherein the doses are administered every other day.

12. A method for infecting an equine in order to produce a model that mimics natural infection comprising administering between about 1 and about 10 median equine infective doses in multiple low dose challenge of an EIAV to equines.

13. The method of claim 12 wherein the administration is repeated.

14. The method of claim 12 wherein the doses are administered every other day.

15. A method for infecting an equine in order to produce a model that mimics natural infection comprising administering less than 300 median equine infective doses in multiple low dose challenge of an EIAV to equines via a route selected from the group consisting of intravenous, intramuscular, intranasal, intraperitoneal, subcutaneous and a combination thereof.

* * * * *